United States Patent

Fujii et al.

[11] Patent Number: 5,980,772
[45] Date of Patent: Nov. 9, 1999

[54] LUBRICANTS FOR AND METHODS OF PROCESSING SYNTHETIC FIBERS

[75] Inventors: Tsukasa Fujii; Michiharu Nagai, both of Aichi, Japan

[73] Assignee: Takemoto Yushi Kabushiki Kaisha, Aichi, Japan

[21] Appl. No.: 09/010,255

[22] Filed: Jan. 21, 1998

[30] Foreign Application Priority Data

Feb. 25, 1997 [JP] Japan .................................. 9-058529

[51] Int. Cl.$^6$ .............................................. D06M 13/292
[52] U.S. Cl. .................................. 252/8.84; 8/133; 8/147; 252/8.81
[58] Field of Search ................................ 252/8.81, 8.84; 8/133, 147; 427/389.9, 394

[56] References Cited

U.S. PATENT DOCUMENTS

| | | | |
|---|---|---|---|
| 3,634,117 | 1/1972 | Wegerhoff et al. | 252/8.84 |
| 3,639,235 | 2/1972 | Karg | 252/8.84 |
| 3,652,419 | 3/1972 | Karg | 252/8.84 |
| 3,719,597 | 3/1973 | Wegerhoff et al. | 252/8.84 |
| 3,926,816 | 12/1975 | Cohen et al. | 252/8.84 |
| 4,072,617 | 2/1978 | Jahn | 252/8.84 |
| 4,220,611 | 9/1980 | Wolf | 252/8.84 |
| 5,151,218 | 9/1992 | Haubennestel et al. | 252/351 |

OTHER PUBLICATIONS

Chemical Abstract No. 86:107930, abstract of Japanese Patent Specification No. 51–143725, Dec. 1976.
Chemical Abstract No. 90:7543, abstract of Japanese Patent Specification No. 53–103099, Sep. 1978.
Chemical Abstract No. 104:131417, abstract of Japanese Patent Specification No. 60:194177, Oct. 1985.
Chemical Abstract No. 123:85861, abstract of Soviet Union Patent Specification No. 1817794, May 1993.
Chemical Abstract No. 126:212256, abstract of Japanese Patent Specification No. 09–020789, Jan. 1997.
Chemical Abstract No. 108:57842, abstract of Japanese Patent Specification No. 62–069881, Mar. 1987.
Chemical Abstract No. 115:10781, abstract of Japanese Patent Specification No. 03–000871, Oct. 1991.
Chemical Abstract No. 121:37606, abstract of Japanese Patent Specification No. 05–339875, Dec. 1993.
Chemical Abstract No. 121:303020, abstract of Japanese Patent Specification No. 06–158538, Jun. 1994.
Chemical Abstract No. 122:216487, abstract of Japanese Patent Specification No. 06–228885, Aug. 1994.
Chemical Abstract No. 123:115244, abstract of Japanese Patent Specification No. 06–346368, Dec. 1994.
Chemical Abstract No. 123:259685, abstract of Japanese Patent Specification No. 07–166433, Jun. 1995.

*Primary Examiner*—Anthony Green
*Attorney, Agent, or Firm*—Majestic, Parsons, Siebert & Hsue P.C.

[57] ABSTRACT

Synthetic fibers can be effectively lubricated by applying a lubricant containing one or more organic phosphoric acid ester compounds such as acidic phosphoric acid ester of the form $$R^1(OCC_5H_{10})_p - O - \underset{OX^1}{\overset{O}{\underset{\|}{P}}} - OH$$

or $$R^2(OA^1)_m(OCC_5H_{10})_q - O - \underset{OX^2}{\overset{O}{\underset{\|}{P}}} - OH$$

where $R^1$, $R^2$, $X^1$ and $X^2$ are each of a specified structure and integers m, p and q satisfy certain conditions.

14 Claims, No Drawings

LUBRICANTS FOR AND METHODS OF PROCESSING SYNTHETIC FIBERS

BACKGROUND OF THE INVENTION

This invention relates to lubricants for and methods of processing synthetic fibers.

During the spinning process of synthetic fibers such as polyamide and polyester fibers, it is important to prevent generation of fuzz and occurrence of yarn breakages. Since synthetic fibers for industrial materials such as tire cords, seat belts and air bags are produced under severe conditions of high temperature and high contact pressure and are likely to generate fuzz and yarn breakages, it is particularly important with such fibers to prevent generation of fuzz and occurrence of yarn breakages. Agents for lubricating such synthetic fibers (herein referred to simply as the lubricants) are therefore required to be capable of providing sufficient lubricity even to synthetic fibers adapted to undergo a spinning process under a severe condition of high temperature and high contact pressure. This invention relates to lubricating agents which can respond to such a demand and also to methods of processing synthetic fibers.

Examples of prior art lubricant proposed for providing lubricity even to synthetic fibers adapted to undergo a spinning process under such severe temperature and pressure conditions include salts of phosphoric acid ester such as (1) salts of phosphoric acid ester derived from alkylene oxide adduct of branched alcohol having a side chain at β (Japanese Patent Publication Tokkai 62-69881), (2) salts of phosphoric acid ester derived from higher alcohol having an alkyl group with 30–50 carbon atoms or alkylene oxide adduct of such higher alcohol (Japanese Patent Publication Tokkai 3-871), and (3) amine salts of phosphoric acid ester obtained by neutralizing acidic phosphoric acid ester derived from ethylene oxide adduct of higher alcohol by using aliphatic amine or ethylene oxide adduct of aliphatic amine (Japanese Patent Publications Tokkai 6-346368 and 7-166433). Also being proposed are methods of using high molecular compounds such as (4) polyester obtained from polyhydroxy compound and dibasic acid having both its ends closed with aliphatic alcohol, its alkylene oxide adduct or aliphatic carboxylic acid (Japanese Patent Publications Tokkai 3-871 and 5-339875), (5) polyoxyalkyleneglycol with average molecular weight greater than 1000 (Japanese Patent Publication Tokkai 6-158538), and (6) alkylene oxide polymers of alkylamine or dialkylamine with average molecular weight 1000–20000 (Japanese Patent Publication Tokkai 6-228885). These prior art lubricants could not provide a high level of lubricity to synthetic fibers, however, and lubricity could be provided only to a very unsatisfactory level in the case of synthetic fibers as industrial materials adapted to be processed under a condition of high temperature and high contact pressure. Thus, generation of fuzz and occurrence of yarn breakage could not be adequately prevented by prior art lubricants.

SUMMARY OF THE INVENTION

The problem to be overcome by the present invention is that prior art lubricants cannot provide lubricity to synthetic fibers to a sufficiently high degree and in particular in the case of industrial synthetic fibers adapted to be processed under conditions of high temperature and high contact pressure such that generation of fuzz and occurrence of yarn breakage could not be effectively prevented.

This invention is based on the discovery by the present inventors that the above and other problems can be obviated by using organic phosphoric acid ester compounds of a specified kind such as acidic phosphoric acid ester of the form

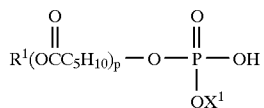

or

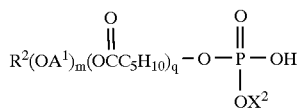

where $R^1$, $R^2$, $X^1$ and $X^2$ are each of a specified structure and integers m, p and q satisfy certain conditions.

DETAILED DESCRIPTION OF THE INVENTION

This invention relates to a lubricating agent, or a lubricant, comprising one or more organic phosphoric acid ester compounds selected from acidic phosphoric acid esters shown by Formula (1) or (2) given below and salts of phosphoric acid ester obtained by neutralizing such acidic phosphoric acid ester with a base, where Formula (1)

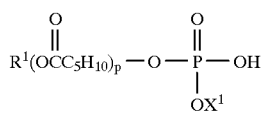

Formula (2)

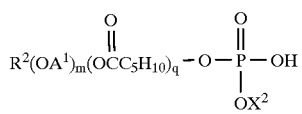

where $X^1$ is hydrogen or a group shown by Formula (3) given below:

Formula (3)

$X^2$ is hydrogen or a group shown by Formula (4) given below:

Formula (4)

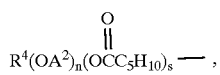

$R^1$, $R^2$, $R^3$ and $R^4$ are each alkyl group with 8–30 carbon atoms or alkenyl group with 8–30 carbon atoms, $A^1$ and $A^2$ are each alkylene group with 2–4 carbon atoms, p, q, r and s are each an integer 3–20, and m and n are each an integer 1–20.

In other words, organic phosphoric acid ester compounds which may be used as a lubricant according to this invention include acidic phosphoric acid esters shown by Formula (1), salts of phosphoric acid ester obtained by neutralizing acidic phosphoric acid ester shown by Formula (1) by a base, acidic phosphoric acid esters shown by Formula (2), and salts of phosphoric acid ester obtained by neutralizing acidic phosphoric acid ester shown by Formula (2) by a base.

Examples of acidic phosphoric acid ester shown by Formula (1) include alkyl poly(oxycarbonylpentyl)dihydrogen phosphate, alkenyl poly(oxycarbonylpentyl)dihydrogen phosphate, bis(alkyl poly(oxycarbonylpentyl)) monohydrogen phosphate, and bis(alkenyl poly(oxycarbonylpentyl))monohydrogen phosphate. They may be obtained by carrying out successive ring-opening addition polymerization of fatty alcohol with ε-caprolactone to obtain ε-caprolactone adduct and then using a phosphation reagent to esterify the hydroxyl group of this ε-caprolactone adduct.

Examples of fatty alcohol for the ring-opening addition polymerization with ε-caprolactone include straight-chain saturated primary alcohols, saturated primary alcohols with side chain and straight-chain saturated secondary alcohols with 8–30 carbon atoms and straight-chain unsaturated primary alcohols with 16–22 carbon atoms. Of these examples, straight-chain saturated primary alcohols with 12–22 carbon atoms, straight-chain saturated secondary alcohols with 12–18 carbon atoms and straight-chain unsaturated primary alcohols with 16–20 carbon atoms having double bond in the molecule are preferred.

The number of moles of added ε-caprolactone in the aforementioned ε-caprolactone adduct of fatty alcohol is 3–20 and preferably 5–18.

Examples of acidic phosphoric acid ester shown by Formula (2) include alkyl poly(oxyalkylene)poly(oxycarbonylpentyl)dihydrogen phosphate, alkenyl poly(oxyalkylene)poly(oxycarbonylpentyl)dihydrogen phosphate, bis(alkyl poly(oxyalkylene)poly(oxycarbonylpentyl))monohydrogen phosphate, and bis(alkenyl poly(oxyalkylene)poly(oxycarbonylpentyl)) monohydrogen phosphate. They may be obtained by carrying out successive ring-opening addition polymerization of fatty alcohol with alkylene oxide to obtain polyalkoxylated fatty alcohol, then carrying out successive ring-opening addition polymerization of this polyalkoxylated fatty alcohol with ε-caprolactone to obtain alkoxypolyether polyester monool and phosphating this alkoxypolyether polyester monool by using a phosphation reagent.

The kind of fatty alcohol to be used for the synthesis of acidic phosphoric acid ester of Formula (2) is the same as that for acidic phosphoric acid ester of Formula (1) discussed above.

Examples of alkylene oxide used for the synthesis of acidic phosphoric acid ester shown by Formula (2) include ethylene oxide, propylene oxide and butylene oxide. Examples of polyalkoxylated fatty alcohol obtained by successive ring-opening addition polymerization of fatty alcohol with alkylene oxide include single alkylene oxide adducts and mixed adducts of two or three alkylene oxides but those obtained by reacting ethylene oxide at a rate of more than 50 molar % are preferred, and those obtained by reacting only ethylene oxide are even more preferred.

The number of moles of added alkylene oxide for these polyalkoxylated fatty alcohols is preferably 1–20 and more preferably 5–15.

In the synthesis of such polyalkoxylated fatty alcohols, aforementioned alkoxy polyether polyester monool is obtained by successive ring-opening addition polymerization of polyalkoxylated fatty alcohol with ε-caprolactone. The number of moles of ε-caprolactone which is added in this case is preferably 3–20 and more preferably 5–18.

Acidic phosphoric acid esters of this invention shown by Formula (1) and (2) are obtained by using aforementioned ε-caprolactone adduct of fatty alcohol or alkoxy polyether polyester monool as starting material and then phosphating it by using a phosphation reagent. This invention does not impose any limitation on the kind of phosphation reagent to be used for this purpose, nor the method of using it. Known methods of using phosphorus oxychloride or phosphoric acid anhydride as phosphation reagent may be used. In such a case, a mixture of monohydrogen phosphate and dihydrogen phosphate is usually obtained as resultant acidic phosphoric acid ester. Such a mixture can be used without separating them for the purpose of this invention.

Lubricants according to this invention are characterized as comprising one or more selected from the aforementioned acidic phosphoric acid esters and salts of phosphoric acid obtained by neutralizing these acidic phosphoric acid esters with a base.

The present invention does not impose any limitation on the kind of base to be used for neutralizing the acidic phosphoric acid ester. Examples of such base to be used include oxides of alkali metals, alkanol amine, N-alkyl alkanol amine, and polyoxyethylene alkylaminoether. Of these, polyoxyethylene alkylaminoether is particularly preferred and polyoxyethylene alkylaminoether with alkyl group with 12–18 carbons atoms and the repetition number of oxyethylene units 5–20 are preferred.

The invention does not impose any limitation on the method of synthesizing the organic phosphoric acid ester compound to be used according to this invention. Any conventionally known methods of synthesis may be used such as (1) the method of carrying out ring-opening addition polymerization of fatty alcohol with ε-caprolactone in the presence of an anionic polymerization catalyst, a cationic polymerization catalyst or a coordination anionic polymerization catalyst to obtain ε-caprolactone adduct of fatty alcohol and then using a phosphation reagent such as phosphoric acid anhydride or phosphorus oxychloride on hydroxyl group of this ε-caprolactone adduct to obtain acidic phosphoric acid ester, (2) the method of carrying out successive ring-opening addition polymerization of fatty alcohol with alkylene oxide in the presence of a basic catalyst to obtain polyalkoxylated fatty alcohol, carrying out ring-opening addition polymerization of the hydroxyl group of this polyalkoxylated fatty alcohol with ε-caprolactone as done in (1) above to obtain alkyl poly(oxyalkylene)poly(oxycarbonylpentyl)monool and thereafter using a phosphation reagent as in (1) on the hydroxyl group of the alkyl poly(oxyalkylene)poly(oxycarbonylpentyl)monool to obtain acidic phosphoric acid ester, and (3) the method of neutralizing the acidic phosphoric acid ester obtained in (1) or (2) above to obtain salts of phosphoric acid ester.

Lubricants according to this invention are characterized as comprising one or more organic phosphoric acid ester compounds selected from acidic phosphoric acid esters and salts of phosphoric acid ester as described above but a known kind of aliphatic acid ester may be used together with such an organic phosphoric acid ester compound.

This invention does not impose any limitation in particular on the kind of aliphatic acid ester which may be used together with an organic phosphoric acid ester. Preferable examples of such aliphatic acid ester include oleic acid esters (esters derived from oleic acid) and oleyl alcohol esters (derived from oleyl alcohol). Particularly preferable examples of oleic acid ester include isopentacosyl oleate and 1,6-hexanediol dioleate and particularly preferable examples of oleyl alcohol ester include dioleyl adipate.

When aliphatic acid ester is used together, this invention does not impose any limitation as to its mixing rate but it is preferable if their weight ratio is inside the range of (aliphatic acid ester)/(organic phosphoric acid ester compound)=50/50–95/5.

When a lubricant according to this invention is applied to synthetic fibers, it is heated to 40–80° C. to make it into a uniform liquid and applied in the neat condition at a rate of 0.1–3.0 weight % with respect to the synthetic fibers. For causing the lubricant according to this invention to adhere to synthetic fibers, known prior art lubricating methods may be used such as the roller oiling method, the guide oiling method and the spray oiling method.

Examples of synthetic fibers to which the lubricants and the processing methods according to this invention can be applied include polyamide filaments, polyester filaments, polyacrylonitrile filaments and polyolefin filaments but it is preferred to apply them to polyamide or polyester filaments. It is particularly preferable to make the application between the spinning process and the drawing process. The methods according to this invention are particularly effective when applied to synthetic fibers which undergo a spinning process under a condition of high temperature and high contact pressure.

Several preferred examples of lubricant will be described next as follows:

(1) Lubricant (T-1) comprising salt of phosphoric acid ester (P-1) obtained by using polyoxyethylene (5 mol) lauryl aminoether to neutralize acidic phosphoric acid ester which is a mixture at molar ratio 1/1 of oleyl poly(oxycarbonylpentyl (p=15)) dihydrogen phosphate ($R^1$=oleyl group; p=15; and $X^1$=hydrogen) and bis (oleyl poly(oxycarbonylpentyl (p, r=15)) monohydrogen phosphate ($R^1$=oleyl group; p=15; $X^1$ as shown by Formula (3) with $R^3$=oleyl group, and r=15);

(2) Lubricant (T-2) comprising salt of phosphoric acid ester (P-2) obtained by using polyoxyethylene (15 mol) stearyl aminoether to neutralize acidic phosphoric acid ester which is a mixture at molar ratio 1/1 of lauryl poly(oxycarbonylpentyl (p=5)) dihydrogen phosphate ($R^1$=lauryl group; p=5; and $X^1$=hydrogen) and bis (lauryl poly(oxycarbonylpentyl (p, r=5)) monohydrogen phosphate ($R^1$=lauryl group; p=5; $X^1$ as shown by Formula (3) with $R^3$=lauryl group, and r=5);

(3) Lubricant (T-3) comprising salt of phosphoric acid ester (P-3) obtained by using dibutyl ethanolamine to neutralize acidic phosphoric acid ester which is a mixture at molar ratio 1/1 of isostearyl poly (oxycarbonylpentyl (p=10)) dihydrogen phosphate ($R^1$=isostearyl group; p=10; and $X^1$=hydrogen) and bis(isostearyl poly(oxycarbonylpentyl (p, r=10)) monohydrogen phosphate ($R^1$=isostearyl group; p=10; $X^1$ as shown by Formula (3) with $R^3$=isostearyl group, and r=10);

(4) Lubricant (T-4) comprising acidic phosphoric acid ester (P-4) which is a mixture at molar ratio 1/1 of stearyl poly(oxycarbonylpentyl (p=10)) dihydrogen phosphate ($R^1$=stearyl group; p=10; and $X^1$=hydrogen) and bis(stearyl poly(oxycarbonylpentyl (p, r=10)) monohydrogen phosphate ($R^1$=stearyl group; p=10; $X^1$ as shown by Formula (3) with $R^3$=stearyl group, and r=10);

(5) Lubricant (T-5) comprising salt of phosphoric acid ester (P-5) obtained by using polyoxyethylene (5 mol) lauryl aminoether to neutralize acidic phosphoric acid ester which is a mixture at molar ratio 1/1 of oleyl poly(oxyethylene (m=5)) poly(oxycarbonylpentyl (q=10)) dihydrogen phosphate ($R^2$=oleyl group; m=5; q=10 and $X^2$=hydrogen) and bis(oleyl poly (oxyethylene (m, n=5) poly(oxycarbonylpentyl (q, s=10)) monohydrogen phosphate ($R^2$=oleyl group; m=5; q=10; $X^2$ as shown by Formula (4) with $R^4$=oleyl group, n=5 and S=10);

(6) Lubricant (T-6) comprising salt of phosphatic acid ester (P-6) obtained by using polyoxyethylene (15 mol) stearyl aminoether to neutralize acidic phosphoric acid ester which is a mixture at molar ratio 1/1 of lauryl poly(oxyethylene (m=10)) poly(oxycarbonylpentyl (q=10)) dihydrogen phosphate ($R^2$=lauryl group; m=10; q=10 and $X^2$=hydrogen) and bis(lauryl poly (oxyethylene (m, n=10) poly(oxycarbonylpentyl (q, s=10)) monohydrogen phosphate ($R^2$=lauryl group; m=10; q=10; $X^2$ as shown by Formula (4) with $R^4$=lauryl group, n=10 and s=10);

(7) Lubricant (T-7) comprising salt of phosphoric acid ester (P-7) obtained by using dibutyl ethanolamine to neutralize acidic phosphoric acid ester which is a mixture at molar ratio 1/1 of isostearyl poly (oxyethylene/oxypropylene (molar ratio=8/2; m=10)) poly(oxycarbonylpentyl (q=15)) dihydrogen phosphate ($R^2$=isostearyl group; m=10; q=15 and $X^2$=hydrogen) and bis(isostearyl poly(oxyethylene/oxypropylene (molar ratio=8/2; m, n=10) poly(oxycarbonylpentyl (q, s=15)) monohydrogen phosphate ($R^2$=isostearyl group; m=10; q=15; $X^2$ as shown by Formula (4) with $R^4$=isostearyl group, n=10 and s=15);

(8) Lubricant (T-8) comprising salt of phosphoric acid ester (P-8) obtained by using potassium hydroxide to neutralize acidic phosphoric acid ester which is a mixture at molar ratio 1/1 of octyl poly(oxyethylene (m=10)) poly(oxycarbonylpentyl (q=10)) dihydrogen phosphate ($R^2$=octyl group; m=10; q=10 and $X^2$=hydrogen) and bis(octyl poly(oxyethylene (m, n=10) poly(oxycarbonylpentyl (q, s=10)) monohydrogen phosphate ($R^2$=octyl group; m=10; q=10; $X^2$ as shown by Formula (4) with $R^4$=octyl group, n=10 and s=10);

(9) Lubricant (T-9) comprising salt of phosphoric acid ester (P-9) which is a mixture at molar ratio 1/1 of stearyl poly(oxyethylene (m=10)) poly (oxycarbonylpentyl (q=10)) dihydrogen phosphate ($R^2$=stearyl group; m=10; q=10 and $X^2$=hydrogen) and bis(stearyl poly(oxyethylene (m, n=10) poly (oxycarbonylpentyl (q, s=10)) monohydrogen phosphate ($R^2$=stearyl group; m=10; q=10; $X^2$ as shown by Formula (4) with $R^4$=stearyl group, n=10 and s=10);

(10) Lubricant (T-10) comprised of 10 parts of aforementioned salt of phosphoric acid ester (P-1) and 90 parts of isopentacosyl oleate;

(11) Lubricant (T-11) comprised of 20 parts of aforementioned salt of phosphoric acid ester (P-2) and 80 parts of 1,6-hexanediol dioleate; and

(12) Lubricant (T-12) comprised of 30 parts of aforementioned salt of phosphoric acid ester (P-7) and 70 parts of dioleyl adipate.

Preferred methods according to this invention of lubricating synthetic fibers include heating a lubricant according to any of (1)–(12) described above to 60° C. to make it a uniform liquid and applying it in the neat condition by the guide oiling method onto polyester fibers immediately after their spinning process at the rate of 1.0 weight %.

The invention is described next by way of test examples for actual applications but these examples are not intended to limit the scope of the invention. Throughout hereafter, "parts" will mean "weight parts" and "%" will mean "weight %".

Test Part No. 1
Synthesis of salts of phosphoric acid ester
Synthesis of (P-1)

ε-caprolactone adduct of oleyl alcohol (15 moles of oxycarbonyl-pentyl unit added to 1 mole of oleyl alcohol, numerical average molecular weight=1950, hydoxyl value= 29) 585 g (0.3 moles) was placed in a flask. While it was kept at 65–70° C. and stirred, phosphoric acid anhydride 14.2 g (0.1 mole) was gradually added over a period of 60 minutes. The reaction was completed after the system was kept for 3 hours at 65–70° C. to obtain acidic phosphoric acid ester. This acidic phosphoric acid ester was analyzed by the potentiometric titration method and found to be an acidic phosphoric acid ester mixture with acid value 28 at molar ratio 1/1 of oleyl poly(oxycarbonylpentyl (p=15)) dihydrogen phosphate and bis(oleyl poly(oxycarbonylpentyl (p, r=15)) monohydrogen phosphate. This acidic phosphoric acid ester mixture 300 g was added gradually into a flask containing polyethoxylated (ethoxy group number=5) laurylamine 61 g (0.15 moles) for neutralization. Although heat of neutralization is generated, the system was kept at 30–50° C. to obtain salt of phosphoric acid ester (P-1).

salts and acidic phosphoric acid esters are summarized in Tables 1 and 2 below.

TABLE 1

| Kind | R$^1$: Group | p | Molar ratio (H/Group of Formula (3)) | R$^3$: Group | r | Base |
|---|---|---|---|---|---|---|
| P-1 | Oleyl | 15 | 1/1 | Oleyl | 15 | B-1 |
| P-2 | Lauryl | 5 | 1/1 | Lauryl | 5 | B-2 |
| P-3 | Isostearyl | 10 | 1/1 | Isostearyl | 10 | B-3 |
| P-4 | Stearyl | 10 | 1/1 | Stearyl | 10 | — |
| R-1 | Oleyl | 1 | 1/1 | Oleyl | 1 | B-1 |
| R-2 | Hexyl | 15 | 1/1 | Hexyl | 15 | B-2 |

In Table 1:
B-1: Polyoxyethylene (OE = 5) lauryl aminoether
B-2: Polyoxyethylene (OE = 15) stearyl aminoether
B-3: Dibutyl ethanolamine

TABLE 2

| Kind | R$^2$ | A$^1$O: Group Kind | m | q | Molar ratio (H/Group of Formula (4)) | R$^4$: Group | A$^2$O: Group Kind | n | s | Base |
|---|---|---|---|---|---|---|---|---|---|---|
| P-5 | Oleyl | EO | 5 | 10 | 1/1 | Oleyl | EO | 5 | 10 | B-1 |
| P-6 | Lauryl | EO | 10 | 10 | 1/1 | Lauryl | EO | 10 | 10 | B-2 |
| P-7 | Isostearyl | EO PO | 8 2 | 15 | 1/1 | Isostearyl | EO PO | 8 2 | 15 | B-3 |
| P-8 | Octyl | EO | 10 | 10 | 1/1 | Octyl | EO | 10 | 10 | B-4 |
| P-9 | Stearyl | EO | 10 | 10 | 1/1 | Stearyl | EO | 10 | 10 | — |
| R-3 | Oleyl | EO | 25 | 10 | 1/1 | Oleyl | EO | 25 | 10 | B-1 |
| R-4 | Oleyl | EO | 5 | 1 | 1/1 | Oleyl | EO | 5 | 1 | B-1 |
| R-5 | Oleyl | EO | 5 | 25 | 1/1 | Oleyl | EO | 5 | 25 | B-1 |
| R-6 | Hexyl | EO | 5 | 10 | 1/1 | Hexyl | EO | 5 | 10 | B-1 |

In Table 2:
EO: Oxyethylene unit
PO: Oxypropylene unit
B-4: Potassium hydroxide

Synthesis of salts (P-2), (P-3), (P-5)–(P-8) and (R-1)–(R-6)

Salts of phosphoric acid ester (P-2), (P-3), (P-5)–(P-8) and (R-1)–(R-6) were synthesized as explained above for the synthesis of (P-1).
Synthesis of acidic phosphoric acid ester (P-4)

ε-caprolactone adduct of stearyl alcohol (10 moles of oxycarbonyl-pentyl unit added to 1 mole of stearyl alcohol, numerical average molecular weight=1400, hydoxyl value= 40) 420 g (0.3 moles) was placed in a flask. While it was kept at 65–70° C. and stirred, phosphoric acid anhydride 14.2 g (0.1 mole) was gradually added over a period of 60 minutes. The reaction was completed after the system was kept for 3 hours at 65–70° C. to obtain acidic phosphoric acid ester. This acidic phosphoric acid ester was analyzed by the potentiometric titration method and found to be an acidic phosphoric acid ester mixture with acid value 55 at molar ratio 1/1 of stearyl poly(oxycarbonylpentyl (p=10)) dihydrogen phosphate and bis(stearyl poly(oxycarbonylpentyl (p, r=10)) monohydrogen phosphate. This will be referred to as acidic phosphoric acid ester (P-4).
Synthesis of acidic phosphoric acid ester (P-9)

Acidic phosphoric acid ester (P-9) was synthesized as explained above for the synthesis of (P-4). Details of these Test Part No. 2
Preparation of lubricants
Preparation of lubricants (T-1)–(T-9) and (t-1)–(t-10)

The salts of phosphoric acid ester and acidic phosphoric acid esters obtained in Test Part No. 1 were directly used as lubricants as they were.
Preparation of lubricants (T-10)–(T-12)

Salt of phosphoric acid ester (P-1), obtained in Test Part No. 1, 10 parts and isopentacosyl oleate 90 parts were mixed together at 70–80° C. until they became uniform to prepare lubricant (T-10). Lubricants (T-11) and (T-12) were similarly prepared. The details of these lubricants are summarized in Table 3.
Test Part No. 3
Application of lubricants to synthetic fibers, measurements and evaluations
Application of lubricants Chips of polyethylene terephthalate with intrinsic viscosity 1.10 and density of carboxyl end group equivalent 15/10$^6$ g were melted and fibers were produced by means of an extruder with the use of spinneret with 500 holes. After the lubricants shown in Table 3 were heated to 60° C. and applied by the guide oiling method by the use of a measuring pump on the fibers from the spinneret, these fibers having the lubricant attached thereon were collected by means of a guiding means. After they were pulled by a draft roll with surface velocity of 3500 m/minute, they were drawn through a first drawing roll, a second drawing roll, a third drawing roll and a relaxing roll such that the total draw ratio would be 1.7. The fineness of the fibers after passing over the relaxing roll was 1500 denier. They were then wound up in the form of a wound cheese of 10 kg to obtain processed synthetic fibers.

Measurements

Amounts of lubricants attached to the fibers were measured according to JIS-L1073 (Test method of synthetic fiber filaments) by using a mixed solvent of (normal hexane)/(ethanol)=50/50 (in volume ratio) as extraction solvent. The results are shown in Table 3.

Evaluations of yarn breakages

The number of yarn breakages per ton of the synthetic fibers was measured and the measured values were evaluated according to the following standard:

A: Yarn breakages less than 0.5 times

B-A: Yarn breakages between 0.5 and 1.0 times

B: Yarn breakages between 1.0 and 1.5 times

C: Yarn breakages between 1.5 and 2.0 times

D: Yarn breakages over 2.0 times

The results are shown in Table 3.

Evaluations of generation of fuzz

The number of surface fuzz of 100 cheeses of the 10 kg wound cheese of the processed synthetic fibers and the measured numbers were evaluated according to the following standard:

A: Less than 50

B-A: Between 50 and 200

B: Between 200 and 500

C: Between 500 and 1000

D: Over 1000

The results are shown in Table 3.

TABLE 3

| | Lubricant | | | | | | |
|---|---|---|---|---|---|---|---|
| Kind | Organic phosphoric ester compound Kind/ Amount | Ester Kind/ Amount | Others Kind/ Amount | Organic phosphoric acid ester compound/ Ester (weight) | Attached amount (%) | Yarn breakage | Fuzz |
| T-1 | P-1 / 100 | - / - | - / - | 100/0 | 1.0 | B-A | B-A |
| T-2 | P-2 / 100 | - / - | - / - | 100/0 | 1.0 | B-A | B-A |
| T-3 | P-3 / 100 | - / - | - / - | 100/0 | 1.0 | B | B-A |
| T-4 | P-4 / 100 | - / - | - / - | 100/0 | 1.0 | B | B |
| T-5 | P-5 / 100 | - / - | - / - | 100/0 | 1.0 | B-A | B-A |
| T-6 | P-6 / 100 | - / - | - / - | 100/0 | 1.0 | B-A | B-A |
| T-7 | P-7 / 100 | - / - | - / - | 100/0 | 1.0 | B | B-A |
| T-8 | P-8 / 100 | - / - | - / - | 100/0 | 1.0 | B | B |
| T-9 | P-9 / 100 | - / - | - / - | 100/0 | 1.0 | B | B |
| T-10 | P-1 / 10 | E-1/90 | - / - | 10/90 | 1.0 | A | A |
| T-11 | P-2 / 20 | E-2/80 | - / - | 20/80 | 1.0 | A | A |
| T-12 | P-7 / 30 | E-3/70 | - / - | 30/70 | 1.0 | A | A |
| t-1 | R-1 / 100 | - / - | - / - | 100/0 | 1.0 | D | C |
| t-2 | R-2 / 100 | - / - | - / - | 100/0 | 1.0 | D | C |
| t-3 | R-3 / 100 | - / - | - / - | 100/0 | 1.0 | C | C |
| t-4 | R-4 / 100 | - / - | - / - | 100/0 | 1.0 | D | C |
| t-5 | R-5 / 100 | - / - | - / - | 100/0 | 1.0 | C | C |
| t-6 | R-6 / 100 | - / - | - / - | 100/0 | 1.0 | C | C |
| t-7 | - / - | - / - | R-7/100 | — | 1.0 | D | D |
| t-8 | - / - | - / - | R-8/100 | — | 1.0 | D | D |
| t-9 | - / - | - / - | R-9/100 | — | 1.0 | D | D |
| t-10 | - / - | - / - | R-10/100 | — | 1.0 | D | D |

In Table 3:
E-1: Isopentacosyl oleate
E-2: 1,6-hexanediol dioleate
E-3: Dioleyl adipate
R-7: Mixture of 33 parts of polyester with average molecular weight 6000 obtainable by polymerization reaction of (polyethoxylated (25) hydrogenated castor oil)/(adipic acid)/(dotriacontanoic acid) = 2/1/2 (molar ratio) and 67 parts of hydrogenized castor oil modified with ethylene oxide adduct (oxyethylene repetition unit = 25);
R-8: Mixture of 23 parts of polymer with average molecular weight 6000 obtainable by polymerization reaction of (hydrogenized castor oil modified with ethylene oxide addition (polyethoxylated (25) hydrogenated castor oil)/(maleic acid anhydride)/(stearic acid) = 2/1/2 (molar ratio) and 77 parts of hydrogenized castor oil modified with ethylene oxide adduct (oxyethylene repetition unit = 25);
R-9: Mixture of 23 parts of polyether copolymer with PO/EO = 25/75 (molar ratio) and average molecular weight 8000 and 77 parts of hydrogenized castor oil modified with ethylene oxide adduct (oxyethylene repetition unit = 25);
R-10: Mixture of 33 parts of polyethoxylated polypropoxylated laurylamine with average molecular weight = 5000 and 67 parts of hydrogenized castor oil modified with ethylene oxide adduct (oxyethylene repetition unit = 25).

It has been clearly shown that this invention makes it possible to provide lubricity even to synthetic fibers produced under a condition of high temperature and high contact pressure and to obtain synthetic fibers which do not generate fuzz or cause yarn breakages even during their spinning process.

What is claimed is:

1. A lubricant for synthetic fibers, said lubricant consisting of one or more organic phosphoric acid ester compounds selected from the group consisting of acidic phosphoric acid esters shown by Formula (1), acidic phosphoric acid esters shown by Formula (2) and salts of phosphoric acid ester obtained by neutralizing any of said acidic phosphoric acid esters, where

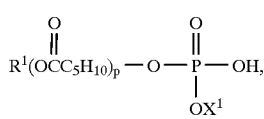
Formula (1)

$$R^1(OCC_5H_{10})_p - O - P(=O)(OH)(OX^1),$$

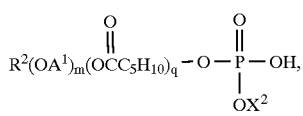
Formula (2)

$$R^2(OA^1)_m(OCC_5H_{10})_q - O - P(=O)(OH)(OX^2),$$

where $X^1$ is hydrogen or a group shown by Formula (3):

Formula (3)

$$R^3(OCC_5H_{10})_r -,$$

$X^2$ is hydrogen or a group shown by Formula (4):

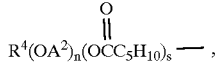
Formula (4)

$$R^4(OA^2)_n(OCC_5H_{10})_s -,$$

$R^1$, $R^2$, $R^3$ and $R^4$ are each alkyl group with 8–30 carbon atoms or alkenyl group with 8–30 carbon atoms, $A^1$ and $A^2$ are each alkylene group with 2–4 carbon atoms, p, q, r and s are each an integer 3–20, and m and n are each an integer 1–20.

2. The lubricant of claim 1 wherein said $R^1$ is selected from the group consisting of residual groups obtained by removing hydroxy group from primary alcohol having 12–22 carbon atoms, residual groups obtained by removing hydroxy group from secondary alcohol having 12–18 carbon atoms, and residual groups obtained by removing hydroxy group from unsaturated alcohol having 16–20 carbon atoms.

3. The lubricant of claim 1 wherein said $R^2$ is selected from the group consisting of residual groups obtained by removing hydroxy group from primary alcohol having 12–22 carbon atoms, residual groups obtained by removing hydroxy group from secondary alcohol having 12–18 carbon atoms, and residual groups obtained by removing hydroxy group from unsaturated alcohol having 16–20 carbon atoms.

4. The lubricant of claim 1 wherein said salt of phosphoric acid ester is a salt obtained by neutralizing acidic phosphoric acid ester with polyoxyethylene alkylaminoether having alkyl group with 12–18 carbon atoms and repetition number of oxyethylene units 5–20.

5. The lubricant of claim 1 wherein said salts of phosphoric acid ester are obtained by neutralizing any of said acidic phosphoric acid esters with a base selected from the group consisting of oxides of alkali metals, alkanol amine, N-alkyl alkanol amine, and polyoxyethylene alkylaminoether.

6. The lubricant of claim 1 wherein said salts of phosphoric acid ester are obtained by neutralizing any of said acidic phosphoric acid esters with polyoxyethylene alkylaminoether with alkyl group with 12–18 carbons atoms and repetition number of oxyethylene units 5–20.

7. A method of processing synthetic fibers, said method comprising the steps of heating a lubricant to 40–80° C. and applying said heated lubricant in a neat condition onto said synthetic fibers at a rate of 0.1–3 weight % between spinning and drawings processes for said synthetic fibers, said lubricant consisting of one or more organic phosphoric acid ester compounds selected from the group consisting of acidic phosphoric acid esters shown by Formula (1), acidic phosphoric acid esters shown by Formula (2) and salts of phosphoric acid ester obtained by neutralizing any of said acidic phosphoric acid esters, where

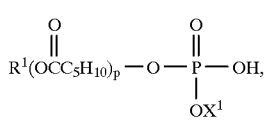
Formula (1)

$$R^1(OCC_5H_{10})_p - O - P(=O)(OH)(OX^1),$$

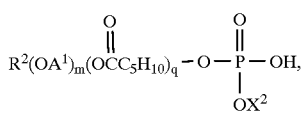
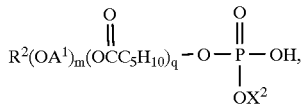
Formula (2)

$$R^2(OA^1)_m(OCC_5H_{10})_q - O - P(=O)(OH)(OX^2),$$

where $X^1$ is hydrogen or a group shown by Formula (3):

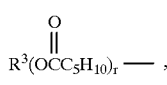
Formula (3)

$$R^3(OCC_5H_{10})_r -,$$

$X^2$ is hydrogen or a group shown by Formula (4):

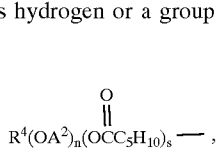
Formula (4)

$$R^4(OA^2)_n(OCC_5H_{10})_s -,$$

$R^1$, $R^2$, $R^3$ and $R^4$ are each alkyl group with 8–30 carbon atoms or alkenyl group with 8–30 carbon atoms, $A^1$ and $A^2$ are each alkylene group with 2–4 carbon atoms, p, q, r and s are each an integer 3–20, and m and n are each an integer 1–20.

8. The method of claim 7 wherein said $R^1$ is selected from the group consisting of residual groups obtained by removing hydroxy group from primary alcohol having 12–22 carbon atoms, residual groups obtained by removing hydroxy group from secondary alcohol having 12–18 carbon atoms, and residual groups obtained by removing hydroxy group from unsaturated alcohol having 16–20 carbon atoms.

9. The method of claim 7 wherein said $R^2$ is selected from the group consisting of residual groups obtained by removing hydroxy group from primary alcohol having 12–22 carbon atoms, residual groups obtained by removing hydroxy group from secondary alcohol having 12–18 carbon atoms, and residual groups obtained by removing hydroxy group from unsaturated alcohol having 16–20 carbon atoms.

10. The method of claim 7 wherein said of phosphoric acid ester is a salt obtained by neutralizing acidic phosphoric acid ester with polyoxyethylene alkylaminoether having alkyl group with 12–18 carbon atoms and repetition number of oxyethylene units 5–20.

11. The method of claim 7 wherein said salts of phosphoric acid ester are obtained by neutralizing any of said acidic phosphoric acid esters with a base selected from the group consisting of oxides of alkali metals, alkanol amine, N-alkyl alkanol amine, and polyoxyethylene alkylaminoether.

12. The method of claim 7 wherein said salts of phosphoric acid ester are obtained by neutralizing any of said acidic phosphoric acid esters with polyoxyethylene alkylaminoether with alkyl group with 12–18 carbons atoms and repetition number of oxyethylene units 5–20.

13. A lubricant for synthetic fibers, said lubricant consisting of one or more organic phosphoric acid ester compounds and one or more aliphatic acid esters;

said organic phosphoric acid ester compounds being selected from the group consisting of acidic phosphoric acid esters shown by Formula (1), acidic phosphoric acid esters shown by Formula (2) and salts of phosphoric acid ester obtained by neutralizing any of said acidic phosphoric acid esters, where

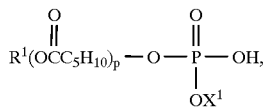

Formula (1)

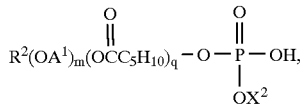

Formula (2)

where $X^1$ is hydrogen or a group shown by Formula (3):

Formula (3)

$X^2$ is hydrogen or a group shown by Formula (4):

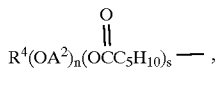

Formula (4)

$R^1$, $R^2$, $R^3$ and $R^4$ are each alkyl group with 8–30 carbon atoms or alkenyl group with 8–30 carbon atoms, $A^1$ and $A^2$ are each alkylene group with 2–4 carbon atoms, p, q, r and s are each an integer 3–20, and m and n are each an integer 1–20;

said aliphatic acid esters being selected from the group consisting of esters derived from oleic acid and esters derived from oleyl alcohol;

the weight ratio of said aliphatic acid esters to said organic phosphoric acid ester compounds in said lubricant being 50/50–95/5.

14. A method of processing synthetic fibers, said method comprising the steps of heating a lubricant to 40–80° C. and applying said heated lubricant in a neat condition onto said synthetic fibers at a rate of 0.1–3 weight % between spinning and drawings processes for said synthetic fibers, said lubricant consisting of one or more organic phosphoric acid ester compounds and one or more aliphatic acid esters;

said organic phosphoric acid ester compounds being selected from the group consisting of acidic phosphoric acid esters shown by Formula (1), acidic phosphoric acid esters shown by Formula (2) and salts of phosphoric acid ester obtained by neutralizing any of said acidic phosphoric acid esters, where

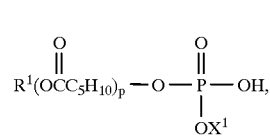

Formula (1)

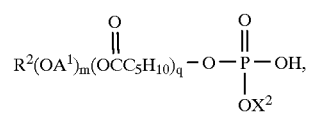

Formula (2)

where $X^1$ is hydrogen or a group shown by Formula (3):

Formula (3)

$X^2$ is hydrogen or a group shown by Formula (4):

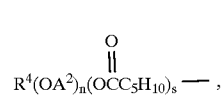

Formula (4)

$R^1$, $R^2$, $R^3$ and $R^4$ are each alkyl group with 8–30 carbon atoms or alkenyl group with 8–30 carbon atoms, $A^1$ and $A^2$ are each alkylene group with 2–4 carbon atoms, p, q, r and s are each an integer 3–20, and m and n are each an integer 1–20;

said aliphatic acid esters being selected from the group consisting of esters derived from oleic acid and esters derived from oleyl alcohol;

the weight ratio of said aliphatic acid esters to said organic phosphoric acid ester compounds in said lubricant being 50/50–95/5.

* * * * *